United States Patent [19]

Kneen et al.

[11] Patent Number: 4,738,986

[45] Date of Patent: Apr. 19, 1988

[54] N-(3-PHENOXYCINNAMYL)ACETOHYDROXAMIC ACID

[75] Inventors: Geoffrey Kneen, High Wycombe; William P. Jackson, Beckenham; Peter J. Islip, Beckenham; Peter J. Wates, Beckenham, all of England

[73] Assignee: Burroughs Wellcome Co., Research Triangle Park, N.C.

[21] Appl. No.: 24,045

[22] Filed: Mar. 10, 1987

Related U.S. Application Data

[62] Division of Ser. No. 838,534, Mar. 11, 1986.

[30] Foreign Application Priority Data

| Mar. 16, 1985 | [GB] | United Kingdom | 8506870 |
| Mar. 16, 1985 | [GB] | United Kingdom | 8506871 |
| Mar. 16, 1985 | [GB] | United Kingdom | 8506872 |

[51] Int. Cl.[4] .................. C07C 83/10; A61K 31/085; A61K 31/185; A01N 3/02
[52] U.S. Cl. ..................................... 514/575; 71/68; 71/118; 260/500.5 H
[58] Field of Search ................. 260/500.5 H; 514/575

[56] References Cited

U.S. PATENT DOCUMENTS

| 3,236,871 | 2/1966 | Hinman et al. | 260/500.5 H |
| 3,306,726 | 2/1967 | Berliner et al. | 71/118 |
| 3,427,316 | 2/1969 | Wakeman et al. | 260/500.5 H |
| 3,439,018 | 4/1969 | Brookes et al. | 260/500.5 H |
| 3,591,623 | 7/1971 | Back et al. | 260/500.5 H |
| 3,691,234 | 9/1972 | Kieter et al. | 260/545 R |
| 3,825,585 | 7/1974 | Chappelow et al. | 260/500.5 H |
| 4,169,720 | 10/1979 | Schacht et al. | 260/500.5 H |
| 4,191,554 | 3/1980 | Gregory | 71/118 |
| 4,405,357 | 9/1983 | Chang | 260/500.5 H |
| 4,604,407 | 8/1986 | Haslanger et al. | 260/500.5 H |
| 4,605,669 | 8/1986 | Summers | 260/500.5 H |
| 4,607,053 | 8/1986 | Karenewsky et al. | 260/500.5 H |
| 4,608,390 | 8/1986 | Summers | 260/500.5 H |
| 4,623,661 | 11/1986 | Summers | 260/500.5 H |

FOREIGN PATENT DOCUMENTS

| 127726 | 1/1984 | European Pat. Off. | |
| 161939 | 11/1985 | European Pat. Off. | |
| 196674 | 10/1986 | European Pat. Off. | |
| 1143265 | 2/1963 | Fed. Rep. of Germany | 260/500.5 H |
| 1576218 | 2/1973 | Fed. Rep. of Germany | 71/118 |
| 1461338 | 11/1966 | France | 260/500.5 H |
| 37-5178 | 6/1962 | Japan | 260/500.5 H |
| 40-23671 | 10/1965 | Japan | 260/500.5 H |
| 50-25730 | 3/1975 | Japan | 71/118 |
| 1136633 | 12/1968 | United Kingdom | 260/500.5 H |

OTHER PUBLICATIONS

Buraczewski et al, "Bulletin De L'Academie Polonaide Des Sciences", Sep. 2, 1964, pp. 626–629, Translation.
Miyagishmia, Chem. Pharm. Bull., vol. 22, 2283, (1974).
James et al "Chem. Abstracts" 97, 178817n.
Stelzig et al, "Chem. Abstracts" 99, 85307x.
Bur-Hoe et al, "Chimie Therapeutique z (1), 39–48, (1967).
Rawson et al, Tetrahedron, vol. 26, 5653 (1970).

Primary Examiner—J. E. Evans
Attorney, Agent, or Firm—Donald Brown

[57] ABSTRACT

Novel compounds of formula (I)

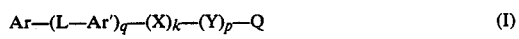

wherein:
k, p and q are independently 0 or 1;
Ar represents either:
  (i) naphthyl, tetrahydronaphthyl, pyridyl or
  (ii) phenyl, optionally substituted,
L is selected from $-(CH_2)_r-$ (where r is 1–4), $-O-$, $-CH_2O-$, $-CH_2S-$, $-OCH_2-$, $-CONH-$, $-NHCO-$, $-CO-$ and $-CH_2NH-$, and,
Ar' represents phenylene, thienylene or pyridylene optionally substituted,
X represents oxygen, sulphur or carbonyl,
Y is $C_{1-10}$ alkylene or $C_{1-10}$ alkenylene;
Q represents a non-cyclic moiety selected from groups of formula

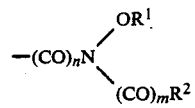

in which one of m and n is 0 and the other is 1, $R^1$ and $R^2$ is selected from hydrogen, $C_{1-4}$ alkyl, amino, $C_{1-4}$ alkylamino, di-$C_{1-4}$ alkylamino, $C_{5-7}$ cycloalkylamino, $C_{5-7}$ cycloalkyl ($C_{1-4}$ alkyl) amino, anilino, N-$C_{1-4}$ alkylanilino
or Q represents a cyclic moiety selected from 1-hydroxy-1,3-dihydroimidazol-2-one and groups of formula

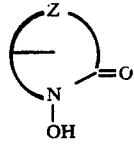

in which Z represents a $C_{2-5}$ alkylene chain in which one of the carbon atoms may be replaced by a hetero atom; and salts thereof.

6 Claims, No Drawings

N-(3-PHENOXYCINNAMYL)ACETOHYDROX-AMIC ACID

This is a division of application Ser. No. 838,534 filed Mar. 11, 1986.

The present invention relates to certain compounds which are hydroxamic acid aryl derivatives, to methods of preparing such compounds, compositions containing them and to their use in medicine and in other applications.

A class of agents defined in European patent specification no. EP 0 055 418 are described therein as dual inhibitors of the lipoxygenase and cyclo-oxygenase enzymes of the mammalian arachidonic acid metabolism and were found to exhibit anti-inflammatory and related activities. Other compounds which have been described as lipoxygenase and/or cyclo-oxygenase inhibitors include certain naphthyloxy derivatives (eg as described in U.S. Pat. No. 3,740,437 or in Proc. Ann. Symp. Inst. Basic Med. Sci, Royal College of Surgeons of England, October 1982, pp 263-274). Compounds described in the latter reference include the compound known as nafazatrom.

We have now found that unexpectedly, subject to the provisos (explicit and implicit) set forth below, the compounds of formula (I) as defined hereinbelow, are particularly advantageous inhibitors of the lipoxygenase and/or cyclooxygenase enzymes and have useful medical prophylactic and therapeutic properties, as well as cerain non-medical uses.

The definition of formula (I)

$$\text{Ar}-(L-\text{Ar}')_q-(X)_k-(Y)_p-Q \qquad (I)$$

is thus:

k, p and q are independently 0 or 1, provided that when k is 1 then p must also be 1;

Ar represents either:
(i) naphthyl, tetrahydronaphthyl or pyridyl, any of which is optionally substituted by one or more substituents independently selected from $C_{1-4}$ alkyl (which may itself optionally be substituted by one or more halogen atoms), $C_{1-4}$ alkoxy, halo, nitro, amino, carboxy, $C_{1-4}$ alkoxycarbonyl and hydroxy, or
(ii) phenyl optionally substituted by one or more substituents idependently selected from phenyl (optionally substituted by one or more substituents independently selected from those specified as optional substituents in (i) above) and said optional substituents specified in (i) above;

L is selected from $-(CH_2)_r-$ (where r is 1-4), $-O-$, $-CH_2O-$, $-CH_2S-$, $-OCH_2-$, $-CONH-$, $-NHCO-$, $-CO-$ and $-CH_2NH-$, and, Ar' represents phenylene, thienylene or pyridylene, any of which may be optionally substituted by one or more substituents independently selected from those specified as optional substituents in definition (i) of Ar;

X represents oxygen, sulphur or carbonyl, provided that at least one atom separates said carbonyl group from any carbonyl group in Q as defined below;

Y is $C_{1-10}$ alkylene or $C_{1-10}$ alkenylene;

Q represents a non-cyclic moiety selected from groups of formula

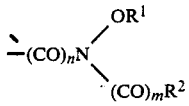

in which one of m and n is 0 and the other is 1, and when n is 1 and m is 0, $R^1$ and $R^2$ are independently selected from hydrogen and $C_{1-4}$ alkyl, with the possibility that $R^2$ can also be $C_{5-7}$ cycloalkyl, or when n is 0 and m is 1, $R^1$ is independently selected from hydrogen, $C_{1-4}$ alkyl, groups as defined for Ar above and groups of formula $-COR^3$ in which $R^3$ is selected from $C_{1-4}$ alkyl (optionally substituted by a carboxy or $C_{1-4}$ alkoxycarbonyl group) and groups of formula $-N(R^4)R^5$ in which $R^4$ is hydrogen or $C_{1-4}$ alkyl and $R^5$ represents hydrogen $C_{1-4}$ alkyl or phenyl optionally substituted by one or more substituents independently selected from those specified as optional substituents in the definition (i) of Ar, and $R^2$ is selected from hydrogen, $C_{1-4}$ alkyl, amino, $C_{1-4}$ alkylamino, di-$C_{1-4}$ alkylamino, $C_{5-7}$ cycloalkylamino, $C_{5-7}$ cycloalkyl ($C_{1-4}$ alkyl) amino, anilino, N—$C_{1-4}$ alkylanilino and groups as defined for Ar above;

or Q represents a cyclic moiety selected from 1-hydroxy-1,3-dihydroimidazol-2-one and groups of formula

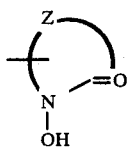

in which Z represents a $C_{2-5}$ alkylene chain in which one of the carbon atoms may be replaced by a hetero atom; and physiologically acceptable salts thereof and salts thereof;

with the proviso that:
when q is 0, k is 0 or 1 and p is 1, Ar is phenyl or naphthyl, either being optionally substituted by one or more substituents as specified in definition (i) of Ar, and X is oxygen or sulphur (in the case when k is 1) Y is $C_{1-10}$ alkylene and Q represents said non-cyclic moiety as hereinbefore defined in which one of $R^1$ and $R^2$ is hydrogen or $C_{1-4}$ alkyl;

then the other of $R^1$ and $R^2$ is neither hydrogen nor $C_{1-4}$ alkyl.

The unexpected advantages we have found in compounds of formula (I) and their salts are selected from one or more of the following, namely: surprisingly high potency, surprising oral efficacy, surprising efficacy by inhalation and surprisingly long duration of action.

It should be appreciated that we make no claim to those compounds of formula (I) and their salts, processes for their preparation, compositions containing them and their use, which are not novel having regard to following references:

(a) Patent Specifications:

EP 0 161 939 A

GB 1 226 344    GB 1 427 114
GB 1 278 739    GB 1 437 783
GB 1 315 830    GB 1 444 492
GB 1 382 996    GB 2 047 234 A

GB 1 396 726

US 3 600 437   US 3 972 934
US 3 821 289   US 3 978 116
US 3 890 377
JP 57035543   JP 57062239
(b) Literature references:
Tetrahedron 1970 26 (23) 5653-64
Fur. J. Med. Chem. Chimica. Therapeutica 1975 10 (2) 125-128
Fur. J. Med. Chem. Chimica. Therapeutica 1970 13 (2) 211-13
J. Chem. Eng. Data 1985 30 237-9
Chem. Biol. Hydroxamic Acids [Proc. Int. Symp.] 1981, 51-62
Arzneim. Forsch. 1978 28 (11) 2087-92

Thus for example, European patent specification 0 161 939 A discloses a genus of compounds which are alleged to be anti-allergic and anti-asthmatic inhibitors of delta-5 lipoxygenase. This genus embraces compounds of formula (I) as hereinbefore defined which inter alia, are excluded by the proviso that:
when Q represents said non-cyclic moiety as hereinbefore defined,
(1) then when n is 1 and m is 0,
when q is 0 and Ar is as definition (ii) or q is 1, Ar is as definition (i) and L is —$CH_2$—, —O— or —$CH_2O$— and Ar' is phenylene optionally substituted as defined,
then at least one of k and p must be 1;
(2) and when n is 0 and m is 1,
when $R^1$ is hydrogen or $C_{1-4}$ alkyl and $R^2$ is phenyl optionally substituted by a single substituent selected from $C_{1-4}$ alkyl, $C_{1-4}$ alkoxy and phenyl optionally substituted by one or more substituents independently selected from these specified as optional substituents in definition (i) of Ar,
then at least one of k and p must be 1, and in the case when k is 0 and p is 1, Y must be $C_{1-10}$ alkenylene.

U.S. Pat. No. 3,600,437 discloses a genus of compounds said to be anti-inflammatory, analgesic and antipyretic agents. This genus embraces compounds of formula (I) as hereinbefore defined which are excluded by the proviso that:
when q and p are 1, k is 0, Ar is unsubstituted phenyl, L is —O—, Q is said non-cyclic moiety as hereinbefore defined, m is 0 and n is 1, L and —$(Y)_p$13 are metasubstituted relative to one another on the Ar', Ar' is phenylene and is unsubstituted or bears a substituent selected from hydroxy, amino, nitro, halo, methyl, ethyl, and $C_{1-3}$ alkoxy and/or a substituent selected from hydroxy, halo, methyl and ethyl, $R^2$ is hydrogen or $C_{1-4}$ alkyl and Y is a group of formula —CH-G—$(CH_2)_s$— in which G is hydrogen or $C_{1-5}$ alkyl and s is 0-3;
then $R^1$ is $C_{1-4}$ alkyl.

The aforementioned U.S. Pat. No. 3,600,437 also discloses inter alia, the individual compound 2-(3-phenoxyphenyl)propionohydroxamic acid.

Throughout this specification, unless indicated to the contrary, alkyl and alkyl-containing moieties (such as alkylene and alkoxy) can be either straight or branched. Alkyl of 1-4 carbon atoms whether alone or part of another moiety comprises methyl, ethyl, n-propyl, iso-propyl, n-butyl, iso-butyl and t-butyl. For use in medicine, the salts of the compounds of formula (I) are those salts which are physiologically acceptable. However, non-physiologically acceptable salts are included within the ambit of the present invention, either for use in non-medical applications such as further described hereinbelow, or as may be used in the preparation of compounds of formula (I) and their physiologically acceptable salts.

When Ar represents optionally-substituted naphthyl, this may represent naphth-1-yl or naphth-2-yl, although the latter is generally preferred.

When Ar represents optionally substituted tetrahydronaphthyl, 5, 6, 7, 8-tetrahydronaphth-1- and -2-yl are preferred, especially -2-yl.

When Ar represents optionally substituted pyridyl, pyrid-2-yl and pyrid-4-yl are preferred.

When q is 1 and Ar' represents optionally substituted phenylene, —L— and —$(X)_k$— are preferably meta- or para-substituted relative to one another on the phenyl ring.

When q is 1 and Ar' represents optionally substituted thienylene, —L— and —$(X)_k$— are preferably attached in the 1- and the 5-positions of the phenylene ring.

When q is 1 and Ar' represents optionally substituted pyridylene, —L— and —$(X)_k$— are preferably attached in the 1- and the 6-positions of the pyridyline ring.

When Q represents a group of formula

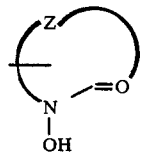

and Z contains a hetero-atom, this may be sulphur, oxygen or nitrogen (—NH—). However, preferably, Z contains 3 carbon atoms. This includes the case when Z does not contain a hetero atom. Of these compounds and salts, especially preferred are those wherein Q represents -5-pyrrolidin-2-one.

One preferred sub-class of the compounds of formula (I) comprises those compounds wherein
q is 0 and p is 1;
Ar represents naphthyl optionally substituted by one or more substituents independently selected from those defined in definition (i) of Ar;
X(in the case when k is 1) is oxygen; and
Q is said non-cyclic moiety as hereinbefore defined in which n is 0, m is 1 and $R^2$ is $C_{1-4}$ alkyl; and salts thereof.

An especially preferred group of compounds and salts within the latter defined sub-class comprises those wherein $R^1$ is hydrogen and $R^2$ is methyl. This group includes compounds and salts wherein Ar is unsubstituted.
q and p are 1 and k is 0.

Another preferred sub-class of the compounds of formula (I) comprises those compounds wherein
Ar represents phenyl optionally substituted by one or more substituents independently selected from those defined in definition (ii) of Ar;
L is —O— or —$CH_2O$—;
Ar' is phenylene optionally substituted by one or more substituents independently selected from those defined in definition (i) of Ar;
and Q is said non-cyclic moiety as hereinbefore defined, provided that when L is —$CH_2O$— and y is $C_{1-6}$ alkenylene, then m is 1 and n is 0; and salts thereof.

An especially preferred group of compounds and salts within the latter defined sub-class comprises those wherein Ar and/or Ar' are substituted only by one or two fluorine atoms or both are unsubstituted, and $R^2$ is $C_{1-4}$ alkyl, particularly methyl. Of this group, meta- or para-relative substitution of L and —$(X)_k$— on Ar' is preferred.

Included within the general class of the compounds of formula (I) and their salts are the following which we may claim separately, namely those wherein:
(i) k is 1 and X represents oxygen;
(ii) k is 1 and X represents sulphur;
(iii) Q represents said non-cyclic moiety and m is 0 and n is 1;
(iv) Q represents said non-cyclic moiety and m is 1 and n is 0;
(v) Q represents a cyclic moiety as hereinbefore defined;
(vi) q is 0;
(vii) q is 1;
(viii) q is 1 and —L— is selected from —O—, —CH$_2$O—, —CH$_2$S—, —NHCO— and —CO—;
(ix) Ar' is optionally substituted phenylene;
(x) Ar' is optionally substituted thienylene;
(xi) Ar' is optionally substituted pyridylene;
(xii) Ar is optionally substituted naphthyl;
(xiii) Ar is optionally substituted tetrahydronaphthyl;
(xiv) Ar is optionally substituted pyridyl;
(xv) k is 0;
(xvi) p is 0;
(xvii) p is 1 and Y is $C_{1-10}$ alkylene;
(xviii) p is 1 and Y is $C_{1-10}$ alkenylene;
(xix) any two or more of (i)-(xviii) together in combination, provided the combination is compatible with the provisos contained within formula (I) as hereinbefore defined.

Preferred compounds of formula (I) include 3-phenoxy-N-methylcinnamohydroxamic acid, N-(3-phenoxycinnamyl)acetohydroxamic acid, N-(4-benzyloxybenzyl)acetohydroxamic acid, N-[2-(5,6,7,8-tetrahydro-2-naphthyloxy)ethyl]acetohydroxamic acid and N-(5,6,7,8-Tetrahydro-2-naphthylallyl)acetohydroxamic acid. Salts of the latter compounds are also preferred.

Examples of other compounds of formula (I) and their salts include the following and salts thereof.
1-Hydroxy-5-[2-(2-naphthyl)ethyl]pyrrolidin-2-one
5,6-Dihydro-N-hydroxy-5-phenyl-1,4-thiazin-3(2H,4H)-one
5,-[2-(4-Biphenyl)ethyl]-1-hydroxy-2-pyrrolidone
5,6-Dihydro-4-hydroxy-6-(1-naphthyl)-1,4-thiazin-3(2H,4H)-one
6-(4-Biphenyl)-5,6-dihydro-4-hydroxy-1,4-thiazin-3(2H,4H)-one
5-(4-Biphenylyl)-1-hydroxy-2-pyrrolidone
1-Hydroxy-5-(4-isobutylphenethyl)-2-pyrrolidone
1-Hydroxy-5-phenethyl-2-pyrrolidone
1-Hydroxy-5-(3-phenylpropyl)-2-pyrrolidone
1-Hydroxy-5-[3-(6-methoxy-2-naphthyl)butyl]-2-pyrrolidone
5,6-Dihydro-4-hydroxy-6-[1-(6-methoxy-2-naphthyl)ethyl]-1,4-thiazin-3-(2H,4H)-one
5-[3-(2-Fluoro-4-biphenyl)butyl]-1-hydroxy-2-pyrrolidone
6-[1-(2-Fluoro-4-biphenyl)ethyl]-5,6-dihydro-4-hydroxy-1,4-thiazin-3(2H,4H)-one
1-Hydroxy-5-[3-(4-isobutylphenyl)butyl]-2-pyrrolidone
5,6-Dihydro-4-hydroxy-6-[1-(4-isobutylphenyl)butyl]-1,4-thiazin-3-(2H,4H)-one
N-[1-(4-biphenylyl)ethyl]acetohydroxamic acid
4-(4-biphenylyl)-N-methyl-4-oxobutanohydroxamic acid
2-(2-fluorobiphenyl-4-yl)-N-methylpropanohydroxamic acid
N-[2-(2-Fluoro-4-biphenylyl)propyl]acetohydroxamic acid
4-(2-Fluoro-4-biphenylyl)-N-methylpentanohydroxamic acid
5-(4-Biphenylyl)-N-methyl5-oxopentanohydroxamic acid
N-[2-(4-Biphenylyloxy)ethyl]acetohydroxamic acid
N-[2-(4-Biphenylyloxy)ethyl]isobutyrohydroxamic acid
N-[3-(4-Biphenylyloxy)propyl]acetohydroxamic acid
2-(4-Biphenylyloxy)-N-methylacetohydroxamic acid
3-(4-Biphenylyloxy)-N-methylpropionohydroxamic acid
7-(4-Biphenylyloxy)-N-methylheptanohydroxamic acid
3-(4-Biphenylyl)-N-methylpropionohydroxamic acid
5-(4-Biphenylyl)-N-methylpentanohydroxamic acid
N-Methyl-2-(5,6,7,8-tetrahydro-1-(or 2-)naphthoxy)acetohydroxamic acid
N-Methyl-3-(5,6,7,8-tetrahydro-1-(or 2-)naphthoxy)propionohydroxamic acid
N-Methyl-7-(5,6,7,8-tetrahydro-1-(or 2-)naphthoxy)heptanohydroxamic acid
Methyl N-methyl-3-(5,6,7,8-tetrahydro-1-(or 2-)naphthoxy)propionohydroxamate
N-[3-(5,6,7,8-tetrahydro-1-(or 2-)naphthoxy)propyl]acetohydroxamic acid
N-[6-(5,6,7,8-tetrahydro-1-(or 2-)naphthoxy)hexyl]acetohydroxamic acid
N-[2-(5,6,7,8-tetrahydro-1-(or 2-)naphthoxy)ethyl]isobutyrohydroxamic acid
N-Methyl-3-(5,6,7,8-tetrahydro-1-(or 2)naphthyl)propionohydroxamic acid
N-Methyl-5-(5,6,7,8-tetrahydro-1-(or 2-)naphthyl)pentanohydroxamic acid
N-[3-(5,6,7,8-tetrahydro-1-(or 2-)naphthyl)propyl]acetohydroxamic acid
N-[5-(5,6,7,8-tetrahydro-1-(or 2-)naphthyl)pentyl]acetohydroxamic acid
N-[3-(5,6,7,8-tetrahydro-1-(or 2-)naphthyl)propyl]isobutyrohydroxamic acid
N-[2-(2-naphthyloxy)ethyl]benzohydroxamic acid
2-Benzyloxy-N-methylbenzohydroxamic acid
N-methyl-3-benzyloxybenzohydroxmic acid
4-benzyloxy-N-methylbenzohydroxamic acid
N-methyl-3-(2-naphthyloxymethyl)benzohydroxamic acid
3-(2-biphenylyloxymethyl)-N-methylbenzohydroxamic acid
4-(4-biphenylyloxymethyl)-N-methylbenzohydroxamic acid
N-methyl-2-[5-methyl-2-(4-methylphenylcarbamoyl)phenoxy]acetohydroxamic acid,
N-[1-(4-benzyloxy-2-hydroxyphenyl)ethyl]-acetohydroxamic acid
N-(2-benzyloxybenzyl)acetohydroxamic acid, viscous oil
2-(3-benzoylphenyl)-N-methylpropionohydroxamic acid
N-methyl-4-(3-propoxybenzoyl)benzohydroxamic acid
N-[4-(1-naphthylmethoxy)benzl]acetahydroxamic acid
N-(3-phenoxybenzyl)acetohydroxamic acid
N-(3-benzyloxybenzyl)acetohydroxamic acid N-methyl-3-(1-naphthyloxymethyl)benzohydroxamic acid
3-benzylamino-N-methylbenzohydroxamic acid
4-benzylamino-N-methylbenzohydroxamic acid
5-benzyloxy-2-hydroxy-N-methylbenzohydroxamic acid
4-benzyloxy-2-hydroxy-N-methylbenzohydroxamic acid
4-benzamido-N-methylbenzohydroxamic acid
3-benzamido-N-methylbenzohydroxamic acid
3-benzoyl-N-methylbenzohydroxamic acid
5-benzoyloxy-N-methylthiophen-2-carbohydroxamic acid
4-benzoyloxy-N-methylthiophen-2-carbohydroxamic acid
3-(biphenyl-2-yloxymethyl)-N-methylbenzohydroxamic acid
N-methyl-3-(1-naphthyl)propenohydroxamic acid
N-methyl-4-methylcinnamohydroxamic acid
2-benzyloxy-N-methylcinnamohydroxamic acid
N-Methyl-3-trifluoromethylcinnamohydroxamic acid
N-Methyl-3-phenoxybenzohydroxamic acid
N-Methyl-4-phenoxybenzohydroxamic acid
2-(4-Biphenylyl)-N-methylpropanohydroxamic acid
N-Methyl-3-(3-propoxybenzoyl)benzohydroxamic acid
N-(Cyclohexyl)-2-[4-(2-methylpropyl)phenyl]-propanohydroxamic acid
N-Methyl-3-(2-naphthyl)propenohydroxamic acid
2-(2-Fluorobiphenyl-4-yl)-N-cyclohexylpropanohydroxamic acid
2-(2-Fluorobiphenyl-4-yl)-N-t-butylpropanohydroxamic acid
N-(1,1-Dimethylethyl)-3-phenoxycinnamohydroxamic acid
2-(4-Biphenylyloxy)-N-methylpropanohydroxamic acid
N-[1-(4-Biphenylyl)ethyl]acetohydroxamic acid
N-(4-Biphenylylmethyl)acetohydroxamic acid
N-[4-(2-Naphthylmethoxy)benzyl]acetohydroxamic acid
N-(4-Phenoxybenzyl)acetohydroxamic acid
N-(4-Benzyloxybenzyl)pivalohydroxamic acid
2-(2-Fluoro-4-biphenylyl)-N-isopropylpropanohydroxamic acid
N-(4-Benzyloxybenzyl)-2-methylpropanohydroxamic acid
N-(4-Phenylcarbamoylbenzyl)acetohydroxamic acid
N-[(2',4'-Difluoro-4-biphenylyl)methyl]acetohydroxamic acid
N-[1-(2',4'-Difluoro-4-biphenylyl)ethyl]-2,2-dimethylpropanohydroxamic acid
N-[4-(4-Biphenylylmethoxy)benzyl]acetohydroxamic acid
N-[4-(2,4-Difluorobenzyloxy)benzyl]acetohydroxamic acid
N-[4-(2,4-Difluorobenzyloxy)benzyl]pivalohydroxamic acid
N-[5,6,7,8-Tetrahydro-2-naphthyl)methyl]acetohydroxamic acid
N-[2-(5,6,7,8-Tetrohydro-2-naphthyloxy)ethyl]-pivalohydroxamic acid
N-(5,6,7,8-Tetrahydro-2-naphthylallyl)pivalohydroxamic acid
N-(5,6,7,8-Tetrahydro-2-naphthylmethyl)pivalohydroxamic acid
N-[2-(2',4'-Difluoro-4-biphenyl)ethylacetohydroxamic acid
N-(4-Isobutylbenzyl)acetohydroxamic acid
N-[1-(4-Biphenyl)ethyl]pivalohydroxamic acid
N-[(4-Biphenylyl)methyl]pivalohydroxamic acid
5-[2-(4-Benxyloxyphenyl)ethyl]-1-hydroxy-2-pyrrolidone
5,6-Dihydro-4-hydroxy-6-(2-naphthyl)-1,4-thiazin-3(2H,4H)-one
6-(4-Benzyloxyphenyl)-5,6-dihydro-4-hydroxy-1,4-thiazin-3(2H,4H)one
1-Hydroxy-1-[2-(2-naphthyloxy)ethyl]-3-phenylurea
N-(4-Benzyloxybenzyl)-N-hydroxy-N-methylurea
3-(4-Benzyloxybenzyl)-1,3-dihydro-1-hydroxyimidazol-2-one
1,3-Dihydro-1-hydroxy-3-(4-phenylbenzyl)imidazol-2-one
N-(4-Benzyloxybenzyl)-O-methylcarbamoylacetohydroxamic acid
N-[2-(2-Naphthylthio)ethyl]-N-(phenylcarbamoyloxy)acetamide
N-[4-(Benzyloxybenzyl)-O-(methylcarbamoyl)-pivalohyroxamic acid
N-(4-Benzyloxybenzyl)-O-(2,2-dimethylethyl)carbamoylacetohydroxamic acid
N-(4-Benzyloxybenzyl)-N-(t-butylcarbonyloxy)acetamide
3-[N-(4-Benzyloxybenzyl)acetamidooxycarbonyl]-propanoic acid
N-[3-(4-Benzyloxyphenyl)prop-2-enyl]acetohydroxamic acid
N-(3-Phenoxycinnamyl)acetohydroxamic acid
N-[2-(4-Biphenylyloxy)ethyl]acetohydroxamic acid
4-(Biphenyl-4-yloxy)-N-methylbut-2-enohydroxamic acid
3-(3-Fluoro-4-phenoxyphenyl)-N-methylprop-2-enohydroxamic acid
N-[3-(4-Benzyloxyphenyl)prop-2-enyl]acetohydroxamic acid
N-[4-(2-Pyridyl)benzyl]acetohydroxamic acid
N-[4-(2,4-Difluorophenoxymethyl)benzyl]acetohydroxamic acid
N-[4-(2-Pyridyloxy)benzyl]acetohydroxamic acid
N-(5-Phenoxymethyl-2-thienylmethyl)acetohydroxamic acid
3-(4-Fluoro-3-phenoxyphenyl)-N-methylprop-2-enohydroxamic acid
N-(6-Phenoxy-2-pyridylmethyl)acetohydroxamic acid
N-[3-(4-Fluoro-3-phenoxyphenyl)prop-2-enyl]acetohydroxamic acid
N-[4-(Benzylthio)benzyl]acetohydroxamic acid
N-[3-(2-Pyridyloxy)benzyl]acetohydroxamic acid
N-[3-(4-Fluoro-3-phenoxyphenyl)prop-2-enyl]-N-hydroxy-N'-methylurea
N-[3-(4-Fluoro-3-phenoxyphenyl)prop-2-enyl]-N-hydroxy-N'-t-butylurea
N-[3-(4-Fluoro-3-phenoxyphenyl)prop-2-enyl]-N-hydroxy-N'-cyclohexylurea
N-[3-(4-Fluoro-3-phenoxyphenyl)prop-2-enyl]-N-hydroxy-N'-phenylurea
N-(Biphenyl-4-ylmethyl)-N-hydroxy-N'-methylurea
N-(Biphenyl-4-ylmethyl)-N-hydroxy-N'-t-butylurea
N-(Biphenyl-4-ylmethyl)-N-hydroxy-N'-cyclohexylurea
N-(Biphenyl-4-ylmethyl)-N-hydroxy-N'-phenylurea
N-Hydroxy-N'-methyl-N-[3-(2-pyridyloxy)benzyl]urea
1-Hydroxy-3-(3-phenoxybenzyl)-1,3-dihydroimidazol-2-one
1-Hydroxy-3-(6-phenoxy-2-pyridylmethyl)-1,3-dihydroimidazol-2-one
3-(2-Pyridyloxy)prop-2-enohydroxamic acid
1-Hydroxy-5-(2-pyridyl)piperazin-2-one N-(2-[4-(2-Pyridylmethoxy)phenoxy]ethyl)acetohydroxamic acid
N-(2-[3-(2-Pyridylmethoxy)phenoxy]ethyl)acetohydroxamic acid
N-(2-[4-(Benzyloxy)phenoxy]ethyl)acetohydroxamic acid
N-[4-Fluoro-2-phenoxyphenyl)methyl]-N-hydroxy-N'-methylurea
N-[4-Fluoro-3-phenoxyphenyl)methyl]-N-hydroxy-N'-phenylurea
N-[3-(Biphenyl-4-yl)prop-2-enyl]-N-hydroxy-N'-methylurea
N-[3-(Biphenyl-4-yl)prop-2-enyl]-N-hydroxy-N'-phenylurea
N-[(4-Benzyloxyphenyl)methyl]-N-hydroxyurea
N-[(4-Benzyloxyphenyl)methyl]-N-hydroxy-N'-methylurea
N-[4-hydroxybenzyloxy)benzyl]acetohydroxamic acid
N-[4-(4-pyridylmethoxy)methyl]acetohydroxamic acid
3-[(4-Fluoro-3-phenoxyphenyl)methyl]-1-hydroxy-1,3-dihydroimidazol-2-one
3-[(2-Fluorobiphenyl-4-yl)methyl]-1-hydroxy-1,3-dihydroimidazol-2-one
1-Hydroxy-3-[3-(4-phenoxyphenyl)prop-2-enyl]-1,3-dihydroimidazol-2-one
3-]4-(4-Fluoro-3-phenoxyphenyl)prop-2-enyl]-1-hydroxy-1,3-dihydroimidazol-2-one Further examples of compounds of formula (1) include each and every specific compound listed below:
N-Methyl-3-(Ar)acrylohydroxamic acid,
N-Methyl-5-(Ar)-2,4-pentadienohydroxamic acid,
N-Methyl-4-(4-isobutylphenyl)-2-butenohydroxamic acid,
N-[3-(Ar)-2-propenyl]acetohydroxamic acid and
N-[3-(Ar)-2-propenyl]isobutyrohydroxamic acid
wherein Ar represents
(i) 1 (or 2)-naphthyl
(ii) 4-isobutylphenyl
(iii) 4-biphenylyl
(iv) 2 (or 3 or 4)-benzyloxyphenyl
(v) phenyl or
(vi) 4-methylphenyl It should be appreciated that any compound in the foregoing list may be claimed alone or with one or more of the others as constituting a preferred aspect of the present invention.

Subject to any limitations expressed implied herein, the present invention also provides any compound of formula (I) (as hereinbefore defined) or physiologically acceptable salt thereof for use as an inhibitor of the lipoxygenase and/or cyclo-oxygenase enzymes of the mammalian arachidonic acid metabolism, to methods of inhibition of such enzyme(s) by administration to a mammal of a lipoxygenase and/or cyclo-oxygenase (as appropriate) inhibiting amount of any such compound or salt, and to use of any such compound or salt in the manufacture of lipoxygenase and/or cyclo-oxygenase inhibitor (as appropriate) agents.

Further, and also subject to any limitations expressed or implied herein, the present invention also provides any compound of formula (I) (as hereinbefore defined) or physiologically acceptable salt thereof, for use as a medical therapeutic and/or prophylactic agent, to methods of medical therapeutic and/or prophylactic treatment by administration to a mammal of a medically therapeutic and/or prophylactic (as appropriate) effective amount of any such compound or salt, and to use of any such compound or salt in the manufacture of medical therapeutic and/or prophylactic (as appropriate) agents. The kinds of medical therapy and prophylaxis pertinent to the foregoing and therefore in that sense comprising part of the present invention, are elaborated by way of example in the following paragraphs which are not intended to be construed as in any way limiting the scope of these aspects of said invention.

By virtue of their lipoxygenase inhibitory properties, said compounds and salts find application in the treatment and/or prophylaxis of any condition where a lipoxygenase inhibitor is indicated, especially spasmogenic and allergic conditions and tumors.

By virtue of their cyclo-oxygenase inhibitory properties, said compounds and salts find application in the treatment and/or prophylaxis of any condition where a cyclo-oxygenase inhibitor is indicated, especially pyresis and pain.

By virtue of both their lipoxygenase and cyclo-oxygenase inhibitory properties, said compounds and salts find application in the treatment and/or prophylaxis of any condition where a dual lipoxygenase/cyclo-oxygenase inhibitor is indicated, especially any condition involving blood platelet aggregation or inflammation. In the case of inflammation, the compounds and salts are particularly suited to the treatment and/or prophylaxis of conditions associated with infiltration of leucocytes into inflamed tissue.

In determining when a lipoxygenase, cyclo-oxygenase or dual lipoxygenase/cyclo-oxygenase inhibitor is indicated, of course inter alia, the particular condition in question and its severity must be taken into consideration and this determination is ultimately at the discretion of the attendant physician.

Examples of the aforesaid spasmogenic conditions are those involving smooth muscle tissue, especially airway smooth muscle constriction such as intrinsic asthma (including intrinsic or idiopathic bronchial asthma and cardiac asthma), bronchitis and arterial smooth muscle constriction such as coronary spasm (including that associated with myocardial infarction, which may or may not lead to left ventricular failure resulting in cardiac asthma) and cerebral spasm or 'stroke'. Other examples include bowel disease caused by abnormal colonic muscular contraction such as may be termed 'irritable bowel syndrome', 'spastic colon' or 'mucous colitis'.

Examples of the aforesaid allergic conditions are extrinsic asthma (from which it will be appreciated that said compounds and salts are particularly favourable as anti-asthmatic agents), allergic skin diseases such as eczema having a total or partial allergic origin, allergic bowel disease (including coeliac disease) and allergic eye conditions such as hayfever (which may additionally or alternatively affect the upper respiratory tract) and allergic conjunctivitis. Examples of the aforesaid tumours are skin neoplasms, both benign and malignant.

Examples of the aforesaid pyretic and painful conditions include fever associated with infections, trauma and injury, malignant disease, and diseases affecting the immune system (including anto-immune disease).

Examples of the aforesaid conditions involving blood platelet aggregation are those resulting from thrombosis, including 'stroke' having a total or partial thrombotic origin, coronary thrombosis, phlebitis and phlebothrombosis (the latter two conditions also possibly being associated with inflammation).

Examples of the aforesaid conditions involving inflammation are inflammatory conditions of the lung, joints, eye, bowel, skin and heart.

Inflammatory lung conditions which may be so treated and/or prevented include asthma and bronchitis (vide supra) and cystic fibrosis (which may also or alternatively involve the bowel or other tissue).

Inflammatory joint conditions which may be so treated and/or prevented include rheumatoid arthritis, rheumatoid spondylitis, osteoarthritis, gouty arthritis and other arthritic conditions.

Inflammatory eye conditions which may be so treated and/or prevented include uveitis (including iritis) and conjunctivitis (vide supra).

Inflammatory bowel conditions which may be so treated and/or prevented include Crohn's disease and ulcerative colitis.

Inflammatory skin diseases which may be so treated and/or prevented include those associated with cell proliferation, such as psoriasis and eczema (vide supra) and dermatitis (whether or not of allergic origin).

Inflammatory conditions of the heart which may be so treated and/or prevented include coronary infarct damage.

Other inflammatory conditions which may be so treated and/or prevented include tissue necrosis of chronic inflammation and tissue rejection following transplant surgery. It is also believed that the compound of formula (I) and their physiologically acceptable salts are effective agents in the prophylaxis and/or treatment of bacterial and fungal infections, this forming a further aspect of the present invention in like manner.

It is known in the literature that some compounds which are cyclo-oxygenase and/or lipoxygenase inhibitors can delay the decay of cut plant matter. Thus, it is now believed that by virtue of their enzyme inhibitory effects, the compounds of formula (I) and salts thereof are also useful for controlling the processes of growth and decay in plants. Thus the present invention also provides the compounds of formula (I) and their salts for use in a method of regulating the growth of, or delaying senescence in vegetable matter by application to said matter of an effective amount of a compound of formula (I) or a salt thereof.

The term senescence refers to the process whereby plant matter decays, especially after being picked, cut or otherwise removed from its normal growing environment. Vegetable matter includes trees, shrubs, flowers and edible vegetables and other food crops.

The above method is particularly applicable to flowers intended for decorative or display purposes such as carnations, crysanthemums, daisies, begonias, etc. These include perennial annual and biannual flowers, for example those that grow from bulbs (eg dahlias) or from seed (eg marigolds). The method is also especially suited to use with decorative shrubs and trees, for example those which are displayed when cut, such as christmas trees.

The compound of formula (I) and their salts may also be used for the preservation of picked fruits.

For medical use, the amount required of a compound of formula (I) or physiologically acceptable salt thereof (hereinafter referred to as the active ingredient) to achieve a therapeutic effect will, of course, vary both with the particular compound, the route of administration and the mammal under treatment and the particular disorder or disease concerned. A suitable dose of a compound of formula (I) or physiologically acceptable salt thereof for a mammal suffering from, or likely to suffer from any condition as described hereinbefore is 0.1 μg–500 mg of base per kilogram bodyweight. In the case of systemic administration, the dose may be in the range 0.5 to 500 mg of base per kilogram bodyweight, the most preferred dosage being 0.5 to 50 mg/kg of mammal bodyweight for example 5 to 25 mg/kg; administered two or three times daily. In the case of topical administration, eg. to the skin or eye, a suitable dose may be in the range 0.1 ng–100 μg of base per kilogram, typically about 0.1 μg/Kg.

In the case of oral dosing for the treatment or prophylaxis of airway smooth muscle constriction, or asthma or bronchitis in general, due to any course, a suitable dose of a compound of formula (I) or physiologically acceptable salt thereof, may be as specified in the preceding paragraph, but most preferably is from is 1 mg to 10 mg of base per kilogram, the most preferred dosage being from 1 mg to 5 mg/kg of mammal bodyweight, for example from 1 to 2 mg/kg. In the case of pulmonary administration for the latter indications, the dose may be in the range of from 2 μg to 100 mg, for example from 20 μg to 0.5 mg, especially 0.1 to 0.5 mg/kg.

While it is possible for an active ingredient to be administered alone, it is preferable to present it as a pharmaceutical formulation comprising a compound of formula (I) or a pharmacologically acceptable acid addition salt thereof and a physiologically acceptable carrier therefor. Such formulations consitute a further feature of the present invention. Conveniently, the active ingredient comprises from 0.1% to 99.9% by weight of the formulation. Conveniently, unit doses of a formulation contain between 0.1 mg and 1 g of the active ingredient. For topical administration, the active ingredient preferably comprises from 1% to 2% by weight of the formulation but the active ingredient may comprise as much as 10% w/w. Formulations suitable for nasal or buccal administration, (such as self-propelling powder dispensing formulations described hereinafter), may comprise 0.1 to 20% w/w, for example 2% w/w of active ingredient.

The formulations, both for veterinary and for human medical use, of the present invention comprise an active ingredient in association with a pharmaceutically acceptable carrier therefor and optionally other therapeutic ingredient(s). The carrier(s) must be 'acceptable' in the sense of being compatible with the other ingredients of the formulations and not deleterious to the recipient thereof.

The formulations include those in a form suitable for oral, pulmonary, ophthalmic, rectal, parenteral (including subcutaneous, intramuscular and intravenous), intraarticular, topical, nasal or buccal administration.

The formulations may conveniently be presented in unit dosage form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units such as capsules, cachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be in the form of a bolus, electuary or paste.

A tablet may be made by compressing or moulding the active ingredient optionally with one or more accessory ingredients. Compressed tablets may be prepared by compressing, in a suitable machine, the active ingredient in a free-flowing form such as a powder or granules, optionally mixed with a binder, lubricant, inert diluent, surface active or dispersing agent. Moulded tablets may be made by moulding, in a suitable machine, a mixture of the powdered active ingredient and a suitable carrier moistened with an inert liquid diluent.

Formulations for rectal administration may be in the form of a suppository incorporating the active ingredient and a carrier such as cocoa butter, or in the form of an enema.

Formulations suitable for parenteral administration conveniently comprise a sterile aqueous preparation of the active ingredient which is preferably isotonic with the blood of the recipient.

Formulations suitable for intra-articular administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for both intra-articular and ophthalmic administration.

Formulations suitable for topical administration include liquid or semi-liquid preparations such as liniments, lotions, applications; oil-in-water or water-in-oil emulsions such as creams, ointments or pastes; or solutions or suspensions such as drops. For example, for ophthalmic administration, the active ingredient may be presented in the form of aqueous eye drops as, for example, a 0.1–1.0% solution. Formulations suitable for administration to the nose or buccal cavity include powder, self-propelling and spray formulations such as aerosols and atomizers. The formulations, when dispersed, preferably have a particle size in the range of 0.1 to 200μ.

A particularly valuable form of a pharmaceutical composition of the present invention, for use in the prophylaxis or treatment of airway smooth muscle constriction, or asthma or bronchitis in general, due to any cause, is one suitable for pulmonary administration via the buccal cavity. Preferably the composition is such that particles having a diameter of 0.5 to 7μ, most preferably 1 to 6μ, containing active ingredient, are delivered into the lungs of a patient. Such compositions are conveniently in the form of dry powders for administration from a powder inhalation device or self-propelling powder-dispensing containers, for example as a self-propelling aerosol composition in a sealed container; preferably the powders comprise particles containing active ingredient of which particles at least 98% by weight have a diameter greater than 0.5μ and at least 95% by number have a diameter less than 7μ. Most desirably at least 95% by weight of the particles have a diameter greater than 1μ and at least 90% by number of particles have a diameter less than 6μ.

The compositions in the form of dry powders preferably include a solid fine powder diluent such as sugar and are conveniently presented in a pierceable capsule, for example of gelatin.

Self-propelling compositions of the invention may be either powder-dispensing compositions or compositions dispensing the active ingredient in the form of droplets of a solution or suspension. Self-propelling powder-dispensing compositions include a liquid propellant having a boiling point of below 65° F. at atmospheric pressure. Generally the propellant may constitute 50 to 99.9% w/w of the composition whilst the active ingredient may constitute 0.1 to 20% w/w, for example about 2% w/w of the composition. The carrier in such compositions may include other constituents, in particular a liquid non-ionic or solid anionic surfactant, or a solid diluent (preferably having a particle size of the same order as of the particles of active ingredient) or both. The surfactant may constitute from 0.01 up to 20% w/w, though preferably it constitutes below 1% w/w of the composition.

Self-propelling compositions wherein the active ingredient is present in solution comprise an active ingredient, propellant and co-solvent, and advantageously an antioxidant stabiliser. The co-solvents may constitute 5 to 40% w/w of the composition, though preferably less than 20% w/w of the composition.

Compositions of the present invention may also be in the form of aqueous or dilute alcoholic solution, optionally a sterile solution, of the active ingredient for use in a nebuliser or atomiser.

Formulations of the present invention may also be in the form of an aqueous or dilute alcoholic solution, optionally a sterile solution, of the active ingredient for use in a nebuliser or atomiser, wherein an accelerated air stream is used to produce a fine mist consisting of small droplets of the solution. Such formulations usually contain a flavouring agent such as saccharin sodium and a volatile oil. A buffering agent and a surface active agent may also be included in such a formulation which should also contain a preservative such as methylhydroxybenzoate.

Other formulations suitable for nasal administration include a coarse powder having a particle size of 20 to 500 microns which is administered in the manner in which snuff is taken i.e. by rapid inhalation through the nasal passage from a container of the powder held close up to the nose.

In addition to the aforementioned ingredients, the formulations of this invention may include one or more additional ingredients such as diluents, buffers, flavouring agents, binders, surface active agents, thickeners, lubricants, preservatives eg. methylhydroxybenzoate (including anti-oxidants), emulsifying agents and the like. Any other therapeutic ingredient may comprise one or more of the following: antibiotic (e.g. anti-bacterial), anti-fungal and anti-viral agents, and anti-histamines (particularly peripherally acting anti-histamines). However, when such other agent(s) are also present, according to another aspect of the invention, the compound of formula (I) or physiologically acceptable salt thereof and the other agent(s), need not necessarily be present as a pharmaceutical formulation as hereinbefore defined, but merely in combination or intimate admixture, i.e. optionally, a pharmaceutically acceptable carrier need not be present. The combination with anti-histamines is particularly favoured for anti-asthmatic use. Such an anti-histamine may be selected from any compound described in European Patent Applications EP 0 859 959 A and EP 0 117 302 A. The amount and dosage regime for such an anti-histamine may be chosen from any of those recited in the latter two European Specifications. Especially preferred are the anti-histamines (E)-3-(6-(3-pyrrolidino-1-(4-tolyl)prop-1E-enyl(-2-pyridyl)acrylic acid and (E)-3-(6-(3-pyrrolidino-1-(4-tolyl)prop-1E-enyl(-2-pyridyl)propionic acid. Another preferred anti-histamine is (E)-1-(4-methylphenyl)-1-(2-pyridyl)-3-pyrrolidinoprop-1-ene, otherwise known as triprolidine.

For delaying senescence of cut or picked plant matter, or for controlling plant growth, the compounds of formula (I) and their salts re preferably presented in a suitable composition, optionally containing one or more other agents for enhancing the freshness of the plants. Such compositions include solutions and suspensions of the compound in a suitable medium such as an aqueous medium.

The compositions may be applied by immersing part (eg the cut end) or whole of the plant or by spraying the plants before ar after cutting or picking, or by application to the root structure before or after picking. The compounds may also be applied by being spread on the soil prior to cutting or picking and conveyed to the plant roots by rainwater, or by other watering means.

When applied in aqueous solution, the compounds may be presented in a concentration of from 1 $\mu$M to 1M, for example 100 $\mu$M to 100 mM. A typical concentration might be about 1 mM.

The compounds of formula (I) and their salts may be prepared by the following process which (subject to any provisos expressed herein) constitutes a further aspect of the present invention:

(a) for the preparation of compounds of formula (I) in which Q represents a non-cyclic moiety (as hereinbefore defined) in which $R^1$ represents hydrogen, reacting a compound of formula (II)

$$R^6NHOH \qquad (II)$$

with a compound of formula (III)

$$R^7-R^8 \qquad (III)$$

(in which one of $R^6$ and $R^7$ is a group $R^2$ as hereinbefore defined and the other is a group of formula Ar—(-L—Ar')$_q$—(X)$_k$—(Y)$_p$— as hereinbefore defined, and $R^8$ is a group capable of reacting with the NH group in the compound of formula (II) thereby to bring about formation of the corresponding hydroxamic acid or derivative thereof);

(b) for the preparation of compounds of formula (I) in which Q represents a non-cyclic moiety (as hereinbefore defined) in which $R^1$ represents hydrogen, n is 1 and m is 0, reacting a compound of formula (IV)

$$Ar-(L-Ar')_q-(X)_k-(Y)_p-CH=O \qquad (IV)$$

(wherein q, k, p, Ar, Ar', L, X and Y are as hereinbefore defined) with Piloty's acid, i.e. the compound of formula PhSO$_2$NHOH, or an appropriate analogue or derivative thereof;

(c) for the preparation of compounds of formula (I) in which Q represents a non-cyclic moiety (as hereinbefore defined) in which $R^1$ represents hydrogen, reacting a compound of formula (V)

$$R^9N(OZ^1)H \qquad (V)$$

(wherein $R^9$ is a group $R^2$ as hereinbefore defined or a group of formula Ar—(L—Ar')$_q$—(X)$_k$—(Y)$_p$— as hereinbefore defined, as appropriate, and $Z^1$ is hydrogen or an appropriate protecting group) with an appropriate acylating agent, and where $Z^1$ is a protecting group, subjecting the reaction product to such conditions and/or reacting with one or more reagents as appropriate to effect removal of said protecting group; or;

(d) for the preparation of compounds of formula (I) in which Q represents a cyclic group as hereinbefore defined, treating a compounds of formula (VI)

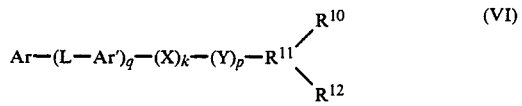

(where Ar, Ar', L, X, Y, q, k and p are as hereinbefore defined and $R^{10}$-$R^{11}$-$R^{12}$ are chosen to be capable of cyclisation) with an agent or agents and under such reaction conditions to bring about cyclisation of said $R^{10}$-$R^{11}$-$R^{12}$;

and optionally if desired, effecting one or more of the following interconversions in any desired order:

(i) when in the compound of formula (I) so formed, any of $R^1$, $R^2$ and (in the definition of $R^1$) $R^4$ and $R^5$ are hydrogen atoms, converting said compound to a corresponding compound of formula (I) wherein any of said hydrogen atoms as desired, are converted to $C_{1-4}$ alkyl groups;

(ii) converting the compound of formula (I) to a corresponding salt thereof;

(iii) when in the compound of formula (I) so formed, n is 0, m is 1 and $R^1$ is hydrogen, converting said compound to a corresponding compound of formula (I) wherein $R^1$ is a group of formula —COR$^3$ as hereinbefore defined;

(iv) when a compound of formula (I), n is 0, m is 1 and $R^1$ is a group of formula —COR$^3$ in which $R^3$ is a $C_{1-4}$ alkyl group substituted by carboxy, converting said compound to a corresponding compound in which $R^3$ is $C_{1-4}$ alkyl substituted by $C_{1-4}$ alkoxycarbonyl.

In process option (a) above, the compound of formula (II) may be used in the form of a salt thereof and the compound of formula (III) for example is an appropriate mixed anhydride or activated acid such as an acid halide (e.g. the chloride). Preferably, the reaction is effected in a suitable solvent and where the compound of formula (II) is in the form of a salt, in the presence of a base, such as an appropriate amine, to liberate the free hydroxylamine compound in situ.

Process option (b) may for example be effected in the presence of a base such as an alkali metal hydroxide or alkoxide, e.g. sodium hydroxide or sodium methoxide.

In process option (c), where the group $Z^1$ in the compound of formula (V) is a protecting group, this may for example be selected from an acetyl, benzyl, O-benzyl, trityl, tetrahydropyranyl, O-tetrahydropyranyl, O-t-butyl and benzoyl. The protecting group may be removed by treatment with acid or base or by hydrogenation as will readily be apparent to those skilled in the art. In general, suitable protecting groups and methods for their removal will be found in T. W. Greene, Protective Groups in Organic Synthesis, Wiley, New York, 1981. Particular examples of removal of such leaving groups include removal of an O-benzyl group by hydrogenolysis over 5% palladium on charcoal at room temperature, or removal of O-tetrahydropyranyl with pyridinium para-toluene sulphate in refluxing methanol.

When process option (c) is a used to prepare a compound of formula (I) wherein Q represents a non-cyclic moiety (as hereinbefore defined) in which n is 0 and m is 1, $R^2$ is an amino group or a mono-amine derivative and $Z^1$ is a protecting group the acylating agent may be an isocyanate of formula (VII).

$$Q^1NCO \tag{VII}$$

(wherein $Q^1$ is said $R^2$ group minus the —NH portion) and the reaction is effected in a suitable solvent such as toluene, optionally at a temperature above ambient.

When process option (c) is used to prepare a compound of formula (I) in which Q represents a non-cyclic moiety (as hereinbefore defined) and $R^2$ is other than as specified in the preceding paragraph (whether Z is hydrogen or a protecting group), the acylating agent may for example be an appropriate mixed anhydride or activated acid, such as an acid halide (for example chloride), When process option (d) is used to prepare a compound of formula (I) in which Q is a group of formula

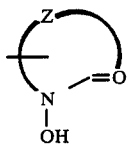

(wherein Z is as hereinbefore defined) one of the groups $R^{10}$ and $R^{12}$ may terminate with a group of formula —$CO_2Q^2$ (where $Q^2$ is hydrogen, amino, $C_{1-6}$ alkyl or aryl (e.g. phenyl)) and the other then terminates with an appropriate reactive group such as a group of formula —$OQ^3$ (wherein $Q^3$ *l is hydrogen or a protecting group such as benzyl or any of those defined above in respect of $Z^1$*) or else the other terminates with a group of formula —$NO_2$ or —NHOH. Generally, the reaction may be effected in a suitable solvent such as toluene, in the presence of an acid catalyst such as para-toluenesulphonic acid, if necessary at an elevated temperature. When one of $R^{10}$ and $R^{12}$ terminates with —NHOH, the reaction may be effected under appropriate reducing conditions, such as in the presence of zinc powder and aqueous ammonium chloride, or with aluminum amalgam.

When process option (d) is used to prepare a compound of formula (I) in which Q is 1-hydroxy-1,3-dihydro-imidazol-2-one, the compound of formula (VI) may be a compound of formula (VIII)

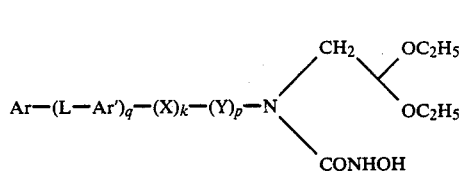

(wherein Ar, Ar', L, X, Y, q, k and p are as hereinbefore defined) and the cyclisation may be initiated by removal of the acetal group with an appropriate reagent such as trifluoroacetic acid.

Optional conversion (i) may for example be effected by reaction with an appropriate alkyl halide or sulphate in the presence of a mild base. Where one or more but not all of a number of hydrogen atoms are to be selectively alkylated, the conversation may require one or more steps of protection and subsequent deprotection.

Optional conversion (ii) conveniently may be effected by reaction with an appropriate organic or mineral acid, or with a base.

Optional conversion (iii) when used for the preparation of compounds wherein $R^3$ is a group of formula —$N(R^4)R^5$, may comprise reacting the compound of formula (I) with an appropriate isocyanate, suitably in an appropriate solvent such as tetrahydrofuran or toluene, optionally in the presence of a catalyst such as 1,8-diazabicyclo[5.4.0]undec-7-ene.

Optional conversion (iii) when used for the preparation of compounds wherein $R^3$ is an alkyl group optionally substituted by a carboxy group or a $C_{1-4}$ alkoxycarbonyl group, may comprise reacting the compound of formula (I) with an appropriate acylating agent such as a mixed anhydride or a suitable activated acid, for example an acid halide such as a chloride. Preferably, the reaction is effected in a solvent such as methylene dichloride or tetrahydrofuran, suitably at from around 0° to ambient temperature.

Optional conversion (iv) may be effected by reaction with the appropriate alcohol in the presence of a suitable mineral acid such as sulphuric.

Salts derived from acids include the acetate, adipate, alginate, aspartate, benzoate, benzenesulphonate, bisulphate, butyrate, citrate, camphorate, camphorsulphonate, cyclopentanepropionate, digluconate, dodecylsulphate, ethanesulphonate, fumarate, glucoheptanoate, glycerophos-phate, hemisulphate, heptanoate, hexanoate, hydrochloride, hydrobromide, hydroiodide, 2-hydroxyethanesulphonate, lactate, maleate, methanesulphonate, 2-naphthalenesulphonate, nicotinate, oxalate, palmoate, pectinate, persulphate, 3-phenyl-propionate, picrate, pivalate, proprionate, succinate, tartrate, thiocyanate, tosylate, and undecanoate.

Base include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine and lysine.

Quaternary ammonium salts can be formed where a nitrogen-containing group is present, for example by reaction with lower alkyl halides, such as methyl, ethyl, propyl, and butyl chlorides, bromides and iodides; dialkyl sulphates, long chain halides such as decyl, lauryl, myristyl and stearyl chlorides, bromides and iodides, aralkyl halides like benzyl and phenethyl bromides.

Thus, subject to the requirements of novelty and inventive step, according to the present invention we may claim (inter alia):

(a) a compound of formula (I) or an acid addition salt thereof;

(b) a method for preparing a compound of formula (I) or a pharmacologically acceptable acid addition salt thereof;

(c) a pharmaceutical formulation comprising a compound of formula (I) or a physiologically acceptable salt thereof and a pharmaceutically acceptable carrier therefor;

(d) a method for preparing such formulations;

(e) a method for the inhibition of the lipoxygenase and-/or cyclooxygenase pathways of the arachidonic acid metabolism by use of a non-toxic, effective, inhibitory amount of a compound of formula (I) or a physiologically acceptable salt thereof;

(f) a method for the prophylaxis or treatment of disease in a mammal, including man, comprising the administration to said mammal of a non-toxic, therapeutically or prophylactically effective amount of a compound of formula (I) or a physiologically acceptable salt thereof;

(g) a method for the prophylaxis or treatment of any individual condition described herein, in a mammal, including man, comprising the administration to said mammal of a non-toxic therapeutically or prophylactically effective amount of a compound of formula (I) or a physiologically acceptable salt thereof;

(h) a method for the prophylaxis or treatment of asthma in a mammal, including man, comprising administration to said mammal of a non-toxic, effective, anti-asthmatic amount of a compound of formula (I) or a physiologically acceptable salt thereof;

(i) a compound of formula (I) or a physiologically acceptable salt thereof for use in medicine, especially as defined in (f)–(h) above.

(j) use of a compound of formula (I) or a physiologically acceptable salt thereof in the manufacture of medical therapeutic agents, particularly those for use as defined in (f)–(h) above;

(k) a method of regulating the growth of, or delaying senescence in vegetable matter by application to said matter of an effective amount of a compound of formula (I) or a salt thereof; or (l) any novel feature described herein.

The following Examples are provided by way of an illustration of the present invention and should in no way be construed as a limitation thereof. All temperatures indicated are in degrees Celsius.

EXAMPLES

Example 1

Preparation of
3-Phenoxy-N-methylcinnamohydroxamic Acid

Methyl chloroformate (2.6 ml) was added dropwise to a solution of m-phenoxycinnamic acid (8 g) and triethylamine (18.5 g) in tetrahydrofuran (60 ml) at 0°. A solution of N-methylhydroxylamine hydrochloride (5.6 g) in water (5 ml) was added, and the mixture was stirred for 2 hours. Isolation with ethyl acetate afforded 3-phenoxy-N-methylcinnamohydroxamic acid (ca 4.3 g), m.pt. 124°–125° [from ethyl acetate/light petroleum (b.pt. 60°–80° C.)]. The m-Phenoxycinnamic acid used as starting material was prepared by condensation of m-phenoxybenzaldehyde with malonic acid in the presence of piperidine and pyridine.

Example 2

Preparation of
2-(2-Fluorobiphenyl-4-yl)-N-methylpropanohydroxamic Acid 2-(2-Fluorobiphenyl-4-yl)propionic acid chloride (prepared in the normal manner from 1.75 g of acid, ca 1 ml of oxalyl chloride, toluene, and 3 drops of N,N-(dimethylformamide) was dissolved in tetrahydrofuran (30 ml) and added over 5–10 minutes to a solution of N-Methylhydroxylamine hydrochloride (ca 2 g) in water (5 ml) containing triethylamine (5 ml) at 0°. Solvent was evaporated, and neutral material was isolated with ethyl acetate. Recrystallization from ether-light petroleum (b.pt. 40°–60°) afforded 2-(2-fluorobiphenyl-4-yl)-N-methylpropanohydroxamic acid (1.25 g), m.pt. 125°–126° C.

Examples 3–24

The following compounds were prepared in a manner generally analogous to the method of Examples 1/2:

(3) 4-(4-Biphenylyl)-N-methyl-4-oxobutanohydroxamic acid, m.pt. 159°–162° C., decomp (4) N-Methyl-3-(1-naphthyl)propenohydroxamic acid, m.pt. 153°–155° C.

(5) N-Methyl-4-methylcinnamohydroxamic acid, m.pt. 140°–142° C.

(6) 2-Benzyloxy-N-methylcinnamohydroxamic acid, m.pt. 99°–100° C.

(7) N-Methyl-3-trifluoromethylcinnamohydroxamic acid, m.pt. 122°–125° C.

(8) N-Methyl-2-[5-methyl-2-(4-methylphenylcarbamoyl)phenoxy]acetohydroxamic acid, m.pt. 191°–192° C.

(9) 2-(3-Benzoylphenyl)-N-methylpropionohydroxamic acid, m.pt. 121°–122° C.

(10) 4-(4-Biphenylyloxymethyl)-N-methylbenzohydroxamic acid, m.pt. 104°–105° C.

(11) N-Methyl-4-(3-propoxybenzoyl)benzohydroxamic acid, m.pt. 107°–108° C.

(12) 4-Benzyloxy-N-methylcinnamohydroxamic acid, m.pt. 181°–182° C.

(13) N-Methyl-3-phenoxybenzohydroxamic acid, m.pt. 71°–72° C.

(14) N-Methyl-4-phenoxybenzohydroxamic acid, m.pt. 92°–93° C.

(15) 2-(4-Biphenylyl)-N-methylpropanohydroxamic acid, m.pt. 125°–127° C.

(16) N-Methyl-3-(3-propoxybenzoyl)benzohydroxamic acid, m.pt. 75°–76° C.

(17) N-(Cyclohexyl)-2-[4-(2-methylpropyl)phenyl]-propanohydroxamic acid, m.pt. 133°–135° C.

(18) 3-(4-Biphenylyl)-N-methylpropenohydroxamic acid, m.pt. 198°–199° C. (preheated)

(19) N-Methyl-3-(2-naphthyl)propenohydroxamic acid, m.pt. 150°–151° C.

(20) 2-(2-Fluorobiphenyl-4-yl)-N-cyclohexylpropanohydroxamic acid, m.pt. 195°–196° C.

(21) 2-(2-Fluorobiphenyl-4-yl)-N-t-butylpropanohydroxamic acid, m.pt. 180°–181° C.)

(22) N-(1,1-Dimethylethyl)-3-phenoxycinnamohydroxamic acid, m.pt. 108°–109° C.

(23) 2-(4-Biphenylyloxy)-N-methylpropanohydroxamic acid, m.pt. 166°–167° C.

(24) N-[3-(4-benzyloxyphenyl)prop-2-enyl]acetohydroxamic acid, m.pt. 148°–149° C.

(25) 4-(Biphenyl-4-yloxy)-N-methylbut-2-enohydroxamic acid

(26) 3-(3-Fluoro-4-phenoxyphenyl)-N-methylprop-2-enohydroxamic acid, m.pt. 150°–152° C.

Example 27

Preparation of
N-(4-Benzyloxybenzyl)acetohydroxamic Acid

Sodium cyanoborohydride (21.3 g) was added in portions to a solution of 4-benzyloxybenzaldehyde oxime (51 g) in acetic acid (250 ml) at ca 50° (cooling). After the reduction was complete, acetic anhydride (22.5 ml) was added in one portion, and the mixture was stirred for 1 hour. The mixture was then poured into water, and the neutral product was isolated with ethyl acetate. The residue was treated with potassium carbonate (2 g) in methanol (400 ml) to hydrolyse the O-acetyl material, then the solvent was evaporated. Addition of 20% citric acid solution (400 ml) and isolation with ethyl acetate furnished N-(4-Benzyloxybenzyl)acetohydroxamic acid (32 g), m.pt. 119°–120° [from ethyl acetate-light petroleum (b.pt. 60°–80°)].

Example 28

Preparation of N-[4-(2-Pyridyloxy)benzyl]acetohydroxamic Acid

2-Bromopyridine (4.74 g) was added to the sodium salt of 4-methylphenol [from 50% sodium hydride (1.58 g) and the phenol (3.56 g)] in dimethyl sulphoxide, and the mixture was stirred for 20 hours at 150° C. Addition of water, and isolation of non-phenolic material with ether gave the pyridyloxy compound (4.81 g). Without purification, this compound (4.74 g) was refluxed in carbon tetrachloride (125 ml) with N-bromosuccinimide (5.02 g) and azo-bisisobutyronitrile initiator (50 mg). After 1 hour (more initiator added after 15 and 30 minutes), the filtered solution was evaporated in vacuo. The crude product (6.76 g) was immediately stirred with O-(tetrahydropyran-2-yl)hydroxylamine (8.99 g) in N,N-dimethylformamide (65 ml) for 65 hours at room temperature. Addition of water and isolation with ether provided the protected hydroxylamine as a viscous oil. Acetylation of the crude protected hydroxylamine (3.84 g) in methylene dichloride (30 ml) was effected with acetic anhydride (1.44 g) for 2 hours at room temperature. Evaporation of solvent, and isolation of non-acidic material with ether furnished the O-protected hydroxamic acid, which was purified by chromatography over silica gel [elution with 1:1 ethyl acetate/light petroleum (b.pt. 60°–80°)](2.61 g).

A mixture of the O-tetrahydroxpyranyl hydroxamic acid (2.6 g) and pyridinium p-toluenesulphonate (191 mg) in methanol (25 ml) was refluxed for 9 hours, then evaporated in vacuo. Isolation with ethyl acetate afforded N-[4-(2-pyridyloxy)benzyl]acetohydroxamic acid (1.42 g), m.pt. 97°–99° C. after recrystallization from ethyl acetate-light petroleum (b.pt. 60°–80°).

Examples 29–69

The following compounds were prepared in a manner generally analogous to the method of Examples 27 and 28:

(29) N-[2-(2-Naphthyloxy)ethyl]benzohydroxamic acid, m.pt. 163°–165° C.
(30) N-[2-(5,6,7,8-Tetrahydro-2-naphthyloxy)ethyl]acetohydroxamic acid, m.pt. 73°–74° C.
(31) N-[1-(4-Biphenylyl)ethyl]acetohydroxamic acid, m.pt. 143°–153° C., vague m.pt.
(32) N-[1-(4-Benzyloxy-2-hydroxyphenyl)ethyl]acetohydroxamic acid, m.pt. 149°–150° C.
(33) N-(2-Benzyloxybenzyl)acetohydroxamic acid, oil
(34) N-(3-Benzyloxybenzyl)acetohydroxamic acid, m.pt. 95°–98° C.
(35) N-(3-Phenoxylbenzyl)acetohydroxamic acid, m.pt. 81°–82° C.
(36) N-(4-Biphenylylmethyl)acetohydroxamic acid, m.pt. 152°–155° C.
(37) N-[4-(1-Naphthylmethoxy)benzyl]acetohydroxamic acid, m.pt. 127°–130° C.
(38) N-[4-(2-Naphthylmethoxy)benzyl]acetohydroxamic acid, m.pt. 161°–14° C.
(39) N-(4-Phenoxybenzyl)acetohydroxamic acid, m.pt. 116°–119° C.
(40) N-(4-Benzyloxybenzyl)pivalohydroxamic acid, m.pt. 143°–144° C.
(41) 2-(2-Fluoro-4-biphenylyl)-N-isopropylpropanohydroxamic acid, m.pt. 151°–152° C.
(42) N-(4-Benzyloxybenzyl)-2-methylpropanohydroxamic acid, m.pt. 113°–115° C.
(43) N-(4-Phenylcarbamoylbenzyl)acetohydroxamic acid, m.pt. 194°–196° C.
(44) N-[(2',4'-Difluoro-4-biphenylyl(methyl]acetohydroxamic acid, m.pt. 134°–135° C.
(45) N-[1-(2',4'-Difluoro-4-biphenylyl)ethyl]-2,2-dimethylpropanohydroxamic acid, m.pt. 152°–153° C.
(46) N-[4-(4-Biphenylylmethoxy)benzyl]acetohydroxamic acid, m.pt. vague, softens 165° C. melts 175° C.
(47) N-[4-(2,4-Difluorobenzyloxy)benzyl]acetohydroxamic acid, m.pt. 113°–115° C.
(48) N-[4-(2,4-Difluorobenzyloxy)benzyl]pivalohydroxamic acid, m.pt. 134°–136° C.
(49) N-[5,6,7,8-Tetrahydro-2-naphthyl)methyl]acetohydroxamic acid, m.pt. 79°–81° C.
(50) N-[2-(5,6,7,8-Tetrohydro-2-naphthyloxy)ethyl]-pivalohydroxamic acid, m.pt. 85°–87° C.
(51) N-(5,6,7,8-Tetrahydro-2-naphthylallyl)acetohydroxamic acid, softens, 95° C. melts, 106°–107° C.
(52) N-(5,6,7,8-Tetrahydro-2-naphthylallyl)pivalohydroxamic acid, m.pt. 144°–145° C.
(53) N-(5,6,7,8-Tetrahydro-2-naphthylmethyl)pivalohydroxamic acid, m.pt. 103°–105° C.
(54) N-[2-(2',4'-Difluoro-4-biphenylyl)ethylacetohydroxamic acid, m.pt. 122°–123° C.
(55) N-(4-Isobutylbenzyl)acetohydroxamic acid, m.pt. 89°–90° C.
(56) N-[1-(4-Biphenyl)ethyl]pivalohydroxamic acid, m.pt. 170°–171° C.
(57) N-[(4-Biphenylyl)methyl]pivalohydroxamic acid, m.pt. 164°–165° C.
(58) N-(3-Phenoxycinnamyl)acetohydroxamic acid, light brown oil
(59) N-[2-(4-Biphenylyloxy)ethyl]acetohydroxamic acid, m.p.t. 125°–127° C.
(60) N-[3-(4-Benzyloxyphenyl)prop-2-enyl]acetohydroxamic acid, m.pt. 148°–149° C.
(61) N-[4-(2-Pyridyl)benzyl]acetohydroxamic acid, m.pt. 134°–135° C. (softens ca 125° C.)
(62) N-[4-(2,4-Difluorophenoxymethyl)benzyl]acetohydrozxamic acid, m.pt. 112°–113° C.
(63) N-[4-(2-Pyridyloxy)benzyl]acetohydroxamic acid, m.pt. 97°–99° C.
(64) N-(5-Phenoxymethyl-2-thienylmethyl)acetohydroxamic acid, m.pt. 103°–104° C.
(65) 3-(4-Fluoro-3-phenoxyphenyl)-N-methylprop-2-enohydroxamic acid, m.pt. 150°–152° C.
(66) N-(6-Phenoxy-2-pyridylmethyl)acetohydroxamic acid
(67) N-[3-(4-Fluoro-3-phenoxyphenyl)prop-2-enyl]acetohydroxamic acid
(68) N-[4-(Benzylthio)benzyl]acetohydroxamic acid
(69) N-[3-(2-Pyridyloxy)benzyl]acetohydroxamic acid Example 70

Preparation of 5-[2-(4-Biphenylyl)ethyl]-1-hydroxy-2-pyrrolidinone

Methyl-1-(4-biphenylyl)-2-oxobutanoate (1.48 g) in ethanol (40 ml) with hydroxylamine hydrochloride (0.348 g) and sodium acetate (0.41 g) was stirred for 16 hours at ambient temperature. Dilution with water precipitated the oxime (1.368 g) which was dissolved (without purification) in acetic acid (15 ml) and treated with sodium cyanoborohydride (0.41 g) under nitrogen. The mixture was stirred for 3 hours at room temperature, then non-acidic material was isolated with ethyl acetate. The resulting crude hydroxylamine in toluene (25 ml) containing p-toluenesulphonic acid catalyst (80 mg) was heated for 1.25 hours at 100° to precipitate 5-[2-(4-Biphenylyl)ethyl]-1-hydroxy-2-pyrrolidinone (0.875 g), m.pt. 192°–194° C. after recrystallization from methanol.

Examples 71–75

The following compounds were prepared in a manner generally analogous to that described in Example 70:
(71) 1-Hydroxy-5-[2-(2-naphthyl)ethyl]pyrrolidin-2-one, m.pt. 163°–164° C.
(72) 5-(4-Biphenylyl)-1-hydroxy-2-pyrrolidone, decomp. at 195° C. in preheated apparatus
(73) 1-Hydroxy-5-(2-phenylethyl)-2-pyrrolidinone m.pt. 120°–122° C.
(74) 1-Hydroxy-5-(3-phenylpropyl)-2-pyrrolidinone m.pt. 63°–65° C.
(75) 5-[2-(4-Benxyloxyphenyl)ethyl]-1-hydroxy-2-pyrrolidone, m.pt. 155°–157° C.

Example 76

Preparation of 5,6-Dihydro-1-hydroxy-5-(1-naphthyl)-1,4-thiazin-3(2H, 4H)-one

A solution of methyl mercaptoacetate (2.3 g) in tetrahydrofuran (15 ml) was added dropwise to 1-(1-Naphthyl)-2-nitroethene (4.32 g) and triethylamine (0.219 ml) in tetrahydrofuran (100 ml). The mixture was stirred for 30 minutes at room temperature, then evaporated in vacuo. The residue (6.12 g) was dissolved in saturated aqueous ammonium chloride solution (120 ml) and 95% ethanol (to give homogeneous solution), then stirred while powdered zinc (2.62 g) was added. The mixture was stirred for 30 minutes at room temperature, then concentrated. Isolation with ethyl acetate furnished 5,6-Dihydro-1-hydroxy-5-(1-naphthyl)-1,4-thiazine-3(2H, 4H)-one (2.09 g), m.pt. 155°–157° C. after recrystallization from ethyl acetate.

Examples 77–80

The following compounds were prepared in a manner generally analogous to that described in Example 76:
(77) 5,6-Dihydro-N-hydroxy-phenyl-1,4-thiazin-3(2H, 4H)-one, m.pt. 159°–160° C.
(78) 6-(4-Biphenylyl)-5,6-dihydro-4-hydroxy-1,4-thiazin-3-(2H, 4H)-one, m.pt. 198°–201° C.
(79) 5,6-Dihydro-4-hydroxy-6-(2-naphthyl)-1,4-thiazin-3(2H, 4H)-one, m.pt. 184°–86° C.
(80) 6-(4-Benzyloxyphenyl)-5,6-dihydro-4-hydroxy-1,4-thiazin-3(2H, 4H)one, m.pt. 179°–181° C.

Example 81

Preparation of 1-Hydroxy-1-[2-(2-naphthyloxy)ethyl]-3-phenylurea

A mixture of 2-naphthyloxyacetaldehyde hydrate (9.85 g), benzyloxyamine (5.94 g) and ethanol (100 ml) was stirred overnight under nitrogen to precipitate 11.21 g of the protected oxime, m.pt. 68°–69.5° C. The oxime (10.1 g) in acetic acid (100 ml) was reduced with sodium cyanoborohydride, then the isolated O-benzyl hydroxylamine, without purification, was treated with phenyl isocyanate (1 equivalent) in toluene for 4 hours at 110° C. The product had m.pt. 75°–77° C. after chromatography over silica gel (elution with methylene chloride) and recrystallization from SVM. Hydrogenation of the last-mentioned O-benzylhydroxyurea over 5% palladium on charcoal in ethanol containing a few drops of acetic acid provided 1-Hydroxy-1-[2-(2-naphthyloxy)ethyl]-3-phenylurea, m.pt. 165°–167° C. (from ethanol).

Example 82

Preparation of N-(4-Benzyloxybenzyl)-N-hydroxy-N-methylurea

Sodium cyanoborohydride (1.94 g) was added to 4-Benzyloxybenzaldoxime (3.5 g) in acetic acid (30 ml) under $N_2$, and the mixture was stirred overnight at room temperature. Solvent was evaporated, and the product (4 g) was isolated with ether. Methyl isocyanate (0.88 g) in ether (10 ml) was added dropwise to a solution of the crude hydroxylamine in toluene (100 ml) at 0°, and the mixture was stirred for 3 hours at room temperature to precipitate N-(4-Benzyloxybenzyl)-N-hydroxy-$N^1$-methylurea (2.2 g), m.pt. 152°–154° after recrystallization from ethyl acetate-light petroleum (m.pt. 60°–80°).

Examples 83–91

The following compounds were prepared in a manner generally analogous to that described in Examples 81 and 82:
(83) N-[3-(4-Fluoro-3-phenoxyphenyl)prop-2-enyl]-N-hydroxy-N'-methylurea
(84) N-[3-(4-Fluoro-3-phenoxyphenyl)prop-2-enyl]-N-hydroxy-N'-t-butylurea
(85) N-[3-(4-Fluoro-3-phenoxyphenyl)prop-2-enyl]-N-hydroxy-N'-cyclohexurea
(86) N-[3-(4-Fluoro-3-phenoxyphenyl)prop-2-enyl]-N-hydroxy-N'-phenylurea
(87) N-(Biphenyl-4-ylmethyl)-N-hydroxy-N'-methylurea
(88) N-(Biphenyl-4-ylmethyl)-N-hydroxy-N'-t-butylurea
(89) N-(Biphenyl-4-ylmethyl)-N-hydroxy-N'-cyclohexylurea
(90) N-(Biphenyl-4-ylmethyl)-N-hydroxy-N'-phenylurea
(91) N-Hydroxy-N'-methyl-N-[3-(2-pyridyloxy)benzyl]urea Example 92

Preparation of 3-(4-Benzyloxybenzyl)-1,3-dihydro-1-hydroxyimidazol-2-one

A mixture of 4-benzyloxybenzaldehyde (9.1 g), aminoacetaldehyde diethyl acetal (6.9 g) and p-toluenesulphonic acid (0.5 g) in toluene (250 ml) as refluxed through a Dean-Stark trap until ca 1 ml of water had been collected. Solvent was evaporated in vacuo, and the crude imine was dissolved in acetic acid (100 ml). Sodium cyanoborohydride (3.15 g) was added in portions under nitrogen, and the mixture was stirred until the reaction was complete. Solvent was evaporated in vacuo, and the amine was isolated free of acidic material with ethyl acetate.

To the crude amine (14.15 g) with triethylamine (14 ml) in toluene (40 ml) was added to 12% phosgene in toluene solution (250 ml) to −40°, and the mixture was warmed to room temperature over 1 hour. Solvent was evaporated, and material soluble in ether was dissolved in tetrahydrofuran (150 ml) and treated with triethylamine (25 ml), hydroxylamine hydrochloride (11 g) and water (25 ml). The mixture was stirred for 1 hour, and evaporated in vacuo.

The crude hydroxyurea was isolated with ethyl acetate, then (18 g) dissolved in chloroform (50 ml) and treated with trifluoroacetic acid (25 ml) and water (25 ml). After 1 hour, the precipitated solid was collected and recrystallised from ethanol/N,N-dimethylformamide to give 3-(4-Benzyloxybenzyl)-1,3-dihydro-1-hydroxyimidazol-2-one (6 g) which darkens without melting at greater than 175°.

Examples 93–85

The following compounds were prepared in a manner generally analogous to that described in Example 92:

(93) 1,3-Dihydro-1-hydroxy-3-(4-phenylbenzyl)imidazol-2-one, softens 180° gradually decomposed at to 220° C.

(94) 1-Hydroxy-3-(3-phenoxybenzyl)-1,3-dihydroimidazol-2-one

(95) 1-Hydroxy-3-(6-phenoxy-2-pyridylmethyl)-1,3-dihydroimidazol-2-one

Example 96

Preparation of N-(4-Benzyloxybenzyl)-O-methylcarbamoylacetohydroxamic Acid

A mixture of N-(4-benzyloxybenzyl)acetohydroxamic acid (1.35 g), methyl isocyanate (0.65 g) and 1,8-diazabicyclo [5.4.0] undec-7-ene catalyst (1 drop) in tetrahydrofuran (10 ml) was stirred for 3 hours then left overnight to provide N-(4-benzyloxybenzyl)-O-methylcarbamoylacetohydroxamic acid (1.35 g) m.pt. 101°–102° [from ethyl acetate-light petroleum (b.pt. 60°–80°)].

Example 97–99

The following compounds were prepared in a manner generally analogous to that described in Example 96:

(97) N-[2-(2-Naphthylthio)ethyl]-N-(phenylcarbamoyloxy)acetamide, m.pt. 96°–98° C.

(98) N-[4-(Benzyloxybenzyl)-O-(methylcarbamoyl)-pivalohydroxamic acid, m.pt. 135°–136° C.

(99) N-(4-Benzyloxybenzyl)-O-(2,2-dimethylethyl)carbamoylacetohydroxamic acid, m.pt. 82°–83° C.

Example 100

Preparation of N-(4-Benzyloxybenzyl)-N-(t-butylcarbonyloxy)acetamide

Pivaloylchloride (1.36 ml) was added dropwise to a solution of N-(4-benzyloxybenzyl)acetohydroxamic acid (2.71 g) and triethylamine (1.7 ml) in methylene dichloride (15 ml) and dimethylaminopyridine (100 ml). The mixture was stirred for 2 hours at room temperature, then neutral material was isolated with ether. The product, N-(4-Benzyloxybenzyl)-N-(t-butylcarbonyloxy)acetamide, was a colourless oil.

Example 101

3-[N-(4-Benzyloxybenzyl)acetamidooxycarbonyl]-propanoic acid, m.pt. 102°–105° was prepared in a manner generally analogous to that described in Example 100.

Example 102

Preservation of Cut Flowers

The compound of Example 27 was made up as a 1 mM solution and the cut stem ends of cut carnations were immersed in the resultant solution in order to prolong their freshness.

Pharmaceutical Formulations

In the following formulation Examples, the "Active Ingredient" may be any compound of formula (I) or a physiologically acceptable salt thereof, for example the compound of Example 27.

EXAMPLE A

| Tablet | |
|---|---|
| | In one tablet |
| Active Ingredient | 5.0 mg |
| Lactose | 82.0 mg |
| Starch | 10.0 mg |
| Povidone | 2.0 mg |
| Magnesium Stearate | 1.0 mg |

Mix together the active ingredient, lactose and starch. Granulate the powders using a solution of povidone in purified water. Dry the granules, add the magnesium stearate and compress to produce tablets, 100 mg per tablet.

EXAMPLE B

| Ointment | |
|---|---|
| Active Ingredient | 1.0 g |
| White Soft Paraffin | to 100.0 g |

Disperse the active ingredient in a small volume of the vehicle. Gradually incorporate this into the bulk to produce a smooth, homogeneous product. Fill into collapsible metal tubes.

EXAMPLE C

| Cream for Topical Use | |
|---|---|
| Active Ingredient | 1.0 g |
| Polawax GP 200 | 20.0 g |
| Lanolin Anhydrous | 2.0 g |
| White Beeswax | 2.5 g |
| Methyl Hydroxybenzoate | 0.1 g |
| Distilled Water | to 100.0 g |

Heat the Polawax, beeswax and lanolin together at 60° C. Add a solution of methyl hydroxybenzoate. Homogenise using high speed stirring. Allow the temperature to fall to 50°. Add and disperse the active ingredient. Allow to cool with slow speed stirring.

EXAMPLE D

| Lotion for Topical Use | |
|---|---|
| Active Ingredient | 1.0 g |
| Sorbitan Monolaurate | 0.6 g |
| Polysorbate 20 | 0.6 g |
| Cetostearyl Alcohol | 1.2 g |
| Glycerin | 6.0 g |
| Methyl Hydroxybenzoate | 0.2 g |
| Purified Water B.P. | to 100.00 ml |

The methyl hydroxybenzoate and glycerin were dissolved in 70 ml of the water at 75° C. The sorbitan monolaurate, Polysorbate 20 and cetostearyl alcohol were melted together at 75° C. and added to the aqueous solution. The resulting emulsion was homogenised, allowed to cool with continuous stirring and the active ingredient added as a suspension in the remaining water. The whole was stirred until homogeneous.

EXAMPLE E

| Eye Drops | |
|---|---|
| Active Ingredient | 0.5 g |
| Methyl Hydroxybenzoate | 0.01 g |
| Propyl Hydroxybenzoate | 0.04 g |
| Purified Water B.P. | to 100.00 ml |

The methyl and propyl hydroxybenzoates were dissolved in 70 ml purified water at 75° and the resulting solution then allowed to cool. The active ingredient was added next and the solution made up to 100 ml with purified water. The solution was sterilised by filtration through a membrane filter $0.22\mu$ pore size and packed aseptically into suitable sterile containers.

EXAMPLE F

| Injection Solution | |
|---|---|
| Active Ingredient | 10.0 mg |
| Water for Injections B.P. | to 1.0 ml |

The active ingredient was dissolved in half of the Water for Injections and then made up to volume and sterilised by filtration. The resulting solution was distributed into ampoules under aseptic conditions.

Pulmonary Formulations

In formulations G and H below, the "Active Ingredient" may be any compound of formula (I) or physiologically acceptable salt thereof, for example the compound of Example 1.

EXAMPLE G

| Powder Capsules for Inhalation | |
|---|---|
| Active Ingredient (0.5–7.0 μm powder) | 4 mg |
| Lactose (30–90 μm powder) | 46.0 mg |

The powders were mixed until homogeneous and filled into suitably sized hard gelatin capsules, 50 mg of mixture per capsule.

EXAMPLE H

| Inhalation Aerosol | |
|---|---|
| Active Ingredient (0.5–7.0 μm powder) | 200 mg |
| Sorbitan Trioleate | 100 mg |
| Saccharin Sodium (0.5–7.0 μm powder) | 5 mg |
| Methanol | 2 mg |
| Trichlorofluoromethane | 4.2 g |
| Dichlorodifluoromethane | to 10.0 ml |

The Sorbitan Trioleate and Menthol were dissolved in the Trichlorofluoromethane. The Saccharin Sodium and active ingredient were dispersed in the mixture which was then transferred to a suitable aerosol canister and the Dichlorofluoromethane injected through the valve system. This composition provides 2 mg of active ingredient in each 100 μl dose.

In vitro inhibition of 5-lipoxygenase (LO) and Cyclooxygenase (CO)

Blood from normal aspirin-free volunteers was centrifuged to separate leukocytes from red cells and platelets. The leukocytes were homogenised and 5 μM arachidonic acid added, followed by incubation at 37° for 5 minutes. The reaction was stopped by boiling. Radioimmunoassay was conducted for leukotriene $B_4$ (an LO product) and thromboxane $B_4$ (a CO product). Results were calculated as $IC_{50}$ μM activity against each enzyme and as listed below.

| Compound Example No. | Activity (μM) | |
|---|---|---|
| | CO | LO |
| 1 | 3.0 | <0.1 |

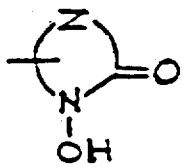

We claim:
1. N-(3-phenoxycinnamyl)acetohydroxamic acid.
2. A salt of N-(3-phenoxycinnamyl)acetohydroxamic acid.
3. A physiologically acceptable salt of N-(3-phenoxycinnamyl)acetohydroxamic acid.
4. A pharmaceutical composition comprising N-(3-phenoxycinnamyl)acetohydroxyamic acid or a physiologically acceptable salt thereof together with a physiologically acceptable carrier therefor.
5. A method of inhibiting lipoxigenase and cyclooxygenase enzymes in a mammal which comprises administering an effective inhibition amount of N-(3-phenoxycinnamyl)acetohydroxamic acid or a physiologically acceptable salt thereof to said mammal.
6. The method of claim 5 in which the mammal is a human.

* * * * *

UNITED STATES PATENT AND TRADEMARK OFFICE
CERTIFICATE OF CORRECTION

PATENT NO. : 4,738,986

DATED : April 19, 1988

INVENTOR(S) : Geoffrey Kneen, William P. Jackson, Peter J. Islip and Peter J. Wates It is certified that error appears in the above-identified patent and that said Letters Patent is hereby corrected as shown below:

Column 2, lines 31 to 36; the formula should appear as follows: 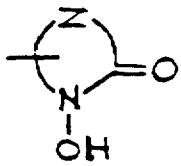

Column 4, lines 27 to 32; the formula should appear as follows: 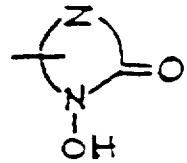

Column 17, lines 28 to 33; the formula should appear as follows: 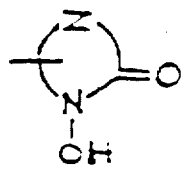

Signed and Sealed this

Twenty-eighth Day of May, 1991

*Attest:*

HARRY F. MANBECK, JR.

*Attesting Officer*   *Commissioner of Patents and Trademarks*

UNITED STATES PATENT AND TRADEMARK OFFICE
CERTIFICATE OF CORRECTION

PATENT NO. : 4,738,986

DATED : April 19, 1988

INVENTOR(S) : Geoffrey Kneen, William P. Jackson, Peter J. Islip and Peter J. Wates It is certified that error appears in the above-identified patent and that said Letters Patent is hereby corrected as shown below:

In the abstract, lines 50 to 56; the formula should appear as follows: